United States Patent [19]

Weider et al.

[11] Patent Number: 5,183,926

[45] Date of Patent: Feb. 2, 1993

[54] PROCESS FOR THE PREPARATION OF AROMATIC DICARBOXYLIC ACIDS AND AROMATIC HYDROCARBONS

[75] Inventors: Richard Weider, Leverkusen; Thomas Scholl, Meerbusch, both of Fed. Rep. of Germany

[73] Assignee: Bayer Aktiengesellschaft, Leverkusen, Fed. Rep. of Germany

[21] Appl. No.: 759,794

[22] Filed: Sep. 13, 1991

Related U.S. Application Data

[63] Continuation of Ser. No. 565,541, Aug. 9, 1990, abandoned.

[30] Foreign Application Priority Data

Aug. 23, 1989 [DE] Fed. Rep. of Germany ....... 3927772

[51] Int. Cl.$^5$ .................... C07C 69/773; C07C 51/16; C07C 1/32; C07C 63/331
[52] U.S. Cl. ...................................... 560/76; 562/419; 562/429; 562/432; 562/480; 562/488; 562/840; 562/867; 568/28; 568/58; 568/635; 585/25; 585/269
[58] Field of Search .................. 560/76; 562/419, 429, 562/432, 480, 488, 840, 867; 568/28, 58, 635; 585/25, 269

[56] References Cited

U.S. PATENT DOCUMENTS

| | | | |
|---|---|---|---|
| 2,712,543 | 7/1955 | Gresham et al. | 562/488 X |
| 2,794,822 | 6/1957 | Schweitzer | 562/488 X |
| 2,823,197 | 2/1958 | Morris et al. | 562/488 X |
| 2,848,486 | 8/1958 | Petropoulos | 562/488 |
| 2,851,437 | 9/1958 | Petropoulos | 562/488 X |
| 3,016,400 | 1/1962 | Petropoulos | 562/488 |
| 3,385,863 | 5/1968 | Wick et al. | 563/488 X |
| 4,485,247 | 11/1984 | Durvasula | 549/310 |
| 4,686,303 | 8/1987 | Bauer et al. | 560/18 |
| 4,698,364 | 10/1987 | Tanemura et al. | 514/563 |
| 4,914,231 | 4/1990 | Manami et al. | 562/429 |

FOREIGN PATENT DOCUMENTS 3743518 7/1989 Fed. Rep. of Germany .

OTHER PUBLICATIONS

The Journal of Organic Chemistry, vol. 37, No. 3, (1972), pp. 425-430.

*Primary Examiner*—José G. Dees
*Assistant Examiner*—Vera C. Clarke
*Attorney, Agent, or Firm*—Sprung, Horn, Kramer & Woods

[57] ABSTRACT

Aromatic dicarboxylic acids of the formula

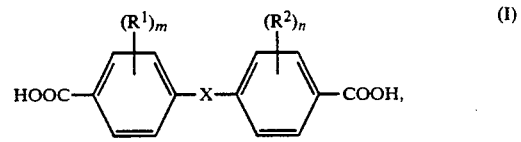

in which
$R^1$, $R^2$, m, n, and X have the meaning mentioned in the description, can be prepared from the bisphenols, on which they are based, of the formula

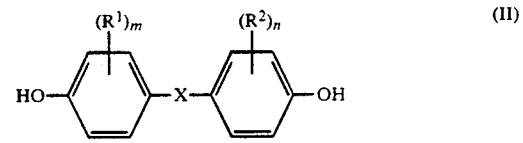

if the bisphenols are first reacted to give the bissulphonates, the sulphonate groups are removed catalytically with $H_2$ and the hydrocarbons obtained in this way are doubly acylated in a known manner and the acyl groups are oxidized to the carboxyl groups.

Many of the aromatic dicarboxylic acids which can be prepared in this way are new.

16 Claims, No Drawings

PROCESS FOR THE PREPARATION OF AROMATIC DICARBOXYLIC ACIDS AND AROMATIC HYDROCARBONS

This application is a continuation, of application Ser. No. 565,541, filed Aug. 9, 1990, now abandoned.

BACKGROUND OF THE INVENTION

1. Field of the Invention

Aromatic carboxylic acids of the type of the formula

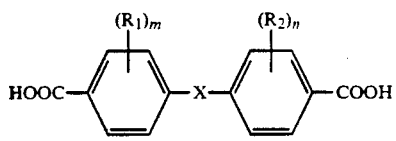

or their acid chlorides and esters are particularly useful intermediates in the polymer sector and are suitable, for example, as monomers for the preparation of polyesters, polyester carbonates or polyamides, having a high heat resistance.

2. Description of the Related Art

Only a few representatives of this type are known, however, owing to the poor accesibility. Thus, in U.S. Pat. No. 2,794,822 the preparation of 2,2-bis-(p-carboxyphenyl)-propane by the following processes is described: Firstly, acetone is reacted with phosphorus pentachloride to give 2,2-dichloropropane (27% yield), which reacts further with benzene in the presence of aluminum chloride to give 2,2-diphenylpropane (46%). This hydrocarbon was then doubly acetylated in the para, para-position with acetyl chloride and aluminum chloride (56%) and the diacetyl product was oxidized with sodium hypochlorite to give 2,2-bis-(p-carboxyphenyl)-propane as the aromatic dicarboxylic acid (89%). The other route described therein, also starting from 2,2-dichloro-propane, leads with toluene in the presence of aluminum chloride to 2,2-bis-(p-tolyl)-propane and oxidation of this with nitric acid in the presence of ammonium vanadate as catalyst leads to the aromatic dicarboxylic acid mentioned. A still further route described in U.S. Pat. No. 2,794,822 leads via the condensation of acetone with aniline to 2,2-bis-(p-aminophenyl)-propane, which is reacted with the aid of sodium nitrite and cyanid ions to give the corresponding dinitrile, which is then hydrolyzed with acid to give the aromatic dicarboxylic acid mentioned.

The processes mentioned proceed with poor yields and are based on the use of poorly accessible geminal dichlorides or highly toxic intermediates and are therefore little suited for industrial application. The processes are additionally greatly restricted with respect to their width of application to homologous compounds.

SUMMARY OF THE INVENTION

The process according to the invention now makes available an improved and widely applicable method for the preparation of aromatic dicarboxylic acids. It starts from the bisphenols, which are available in industrial quantities.

The invention relates to a process for the preparation of aromatic dicarboxylic acids of the formula

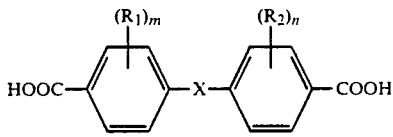

in which
X denotes a single bond, $C_1$-$C_{12}$-alkylene, $C_2$-$C_{12}$-alkylidene, $C_5$-$C_{15}$-cycloalkylene, $C_5$-$C_{15}$-cycloalkylidene, oxygen, sulphur, the sulphone group, the group

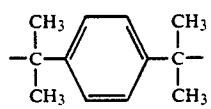

or the group

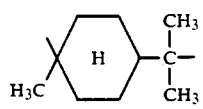

$R^1$ and $R^2$, independently of one another, denote straightchain or branched $C_1$-$C_4$-alkyl or $C_1$-$C_4$-alkoxy and
m and n, independently of one another, represent integers from 0 to 4,
which is characterized in that
a) a bisphenol of the formula

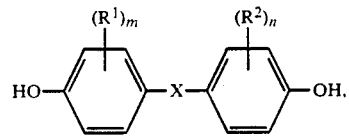

in which
$R^1$, $R^2$, m, n and X have the meaning mentioned, is reacted with a sulphonic acid derivative of the formula $$R^3\text{—}SO_2\text{—}R^4 \qquad (III),$$

in which
$R^3$ represents straight-chain or branched $C_1$-$C_{12}$-alkyl, $C_3$-$C_8$-cycloalkyl, $C_6$-$C_{12}$-aryl or $C_7$-$C_{10}$-aralkyl and
$R^4$ is OH, Cl, Br or O—$O_2$S—$R^3$,
to give a bissulphonate of the formula

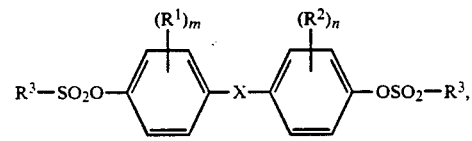

in which
$R^1$, $R^2$, $R^3$, m, n and X have the meaning mentioned,
b) the bissulphonate obtained is hydrogenated in dissolved form at an $H_2$ pressure of 1 to 100 bar, preferably 1 to 50 bar, on a support-containing or support-free hydrogenation catalyst in an amount of from 0.5 to 10 g, preferably 2 to 8 g, of hydrogenation-active component per mole of bissulphonate to give the corresponding hydrocarbon of the formula

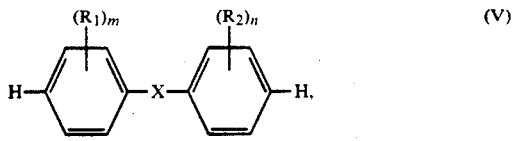

in which

R₁, R₂, m and n have the meaning mentioned, and c) the hydrocarbon obtained is doubly acylated in a known manner and the acyl groups are oxidized to carboxy groups.

The invention further relates to new aromatic dicarboxylic acids of the formula

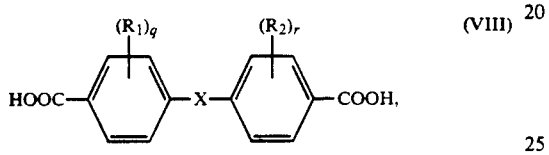

in which $R_1$, $R_2$ and X have the above meaning and q and r have the meanings given below.

The invention further relates to a process for the preparation of the intermediate hydrocarbons of the formula (V) and to new intermediate hydrocarbons of the formula

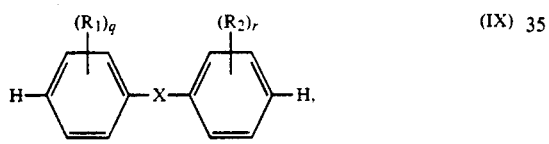

in which $R_1$, $R_2$ and X have the above meaning and q and r have the meaning given below.

DETAILED DESCRIPTION OF THE INVENTION $C_1$–$C_4$-Alkyl is for example, methyl, ethyl, propyl, isopropyl, butyl, isobutyl or tert.-butyl. Straight-chain or branched $C_1$–$C_{12}$-alkyl denotes in addition to the $C_1$–$C_4$-alkyl mentioned amyl, hexyl, octyl, decyl or dodecyl. $C_3$–$C_8$-cycloalkyl is, for example, cyclopropyl, cyclopentyl, cyclohexyl, cyclooctyl, methylcyclopentyl, methylcyclohexyl and the like.

$C_1$–$C_4$-Alkoxy is, for example, methoxy, ethoxy, propoxy, isopropoxy, butoxy, isobutoxy or tert.-butoxy.

$C_1$–$C_{12}$-Alkylene is, for example, methylene, dimethylene, trimethylene, tetramethylene, pentamethylene, hexamethylene, octamethylene, dodecamethylene, but also branched species, such as 1,2-propylene, 1,2- and 1,3-butylene and the like.

$C_2$–$C_{12}$-Alkylidene is, for example, ethylidene, 1,1-propylidene, 2,2-propylidene, 1,1- or 2,2-butylidene, the corresponding hexylidenes, octylidenes or dodecanylidenes.

$C_5$–$C_{15}$-Cycloalkylene is, for example, 1,2- or 1,3-cyclopentylene, 1,2-, 1,3- and 1,4-cyclohexylene, the corresponding derivatives of larger rings and the corresponding alkyl-substituted groups, such as 1,2- or 1,3methylcyclopentanyl, 1,2-, 1,3- and 1,4-methylcyclohexanyl, -dimethyl-cyclohexanyl, -trimethylcyclohexanyl and -tetramethyl-cyclohexanyl, and the corresponding derivatives of larger rings or ethyl, propyl and butyl-substituted groups of this type.

$C_5$–$C_{15}$-Cycloalkylidene corresponds in its scope of meaning to the $C_5$–$C_{15}$-cycloalkylene described, with the difference that the bonds leading to the two aromatic nuclei start from the same ring carbon.

$C_6$–$C_{12}$-Aryl denotes phenyl, p-tolyl, naphthyl or biphenylyl, preferably phenyl or p-tolyl.

$C_7$–$C_{10}$-Aralkyl is, for example, benzyl, phenylethyl, phenylpropyl or phenylbutyl, preferably benzyl.

Preferred bisphenols for the process according to the invention are those of the formula

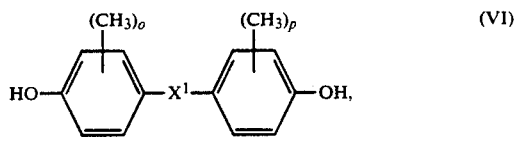

in which $X^1$ denotes methylene, $C_2$–$C_{12}$-alkylidene or $C_5$–$C_{10}$-cycloalklylidene and o and p, independently of one another, represent 0, 1 or 2.

Examples of bisphenols which can be employed according to the invention are: 4,4'-dihydroxy-biphenyl, bis-(4-hydroxyphenyl)-methane, 1,2-bis-(4-hydroxyphenyl)ethane, 1,3-bis-(4-hydroxyphenyl)-propane, 1,7-bis-(4-hydroxyphenyl)-heptane, 1,1-bis-(4-hydroxyphenyl)-ethane, 2,2-bis-(4-hydroxyphenyl)-propane, 1,1-bis-(4-hydroxyphenyl)-butane, 1,1-bis-(4-hydroxyphenyl)-propane, 2,2-bis-(4-hydroxyphenyl)-butane, 1,1-bis-(4-hydroxyphenyl)-2-methylpropane, 2,2-bis-(4-hydroxyphenyl)-pentane, 3,3-bis-(4-hydroxyphenyl)-pentane, 2,2-bis-(4-hydroxyphenyl)-3-methylbutane, 2,2-bis-(4-hydroxyphenyl)-4-methylpentane, 1,1-bis-(4-hydroxyphenyl)-heptane, 4,4-bis-(4-hydroxyphenyl)-2,6-dimethylheptane, 3,3-bis-(4-hydroxyphenyl)-5-methylheptane, 1,1-bis-(4-hydroxyphenyl)-2-ethylhexane, 4,4-bis-(4-hydroxyphenyl)-2,6-dimethylheptane, 2,2-bis-(4-hydroxyphenyl)-undecane, 1,3-bis-(4-hydroxyphenyl)-cyclopentane, 1,3-bis-(4-hydroxyphenyl)cyclohexane, 1,4-bis-(4-hydroxyphenyl)-cyclohexane, 1,1-bis-(4-hydroxyphenyl)-cyclopentane, 1,1-bis-(4-hydroxyphenyl)-cyclohexane, 1,1-bis-(4-hydroxyphenyl)-2-methylcyclohexane, 1,1-bis-(4-hydroxyphenyl)-3-methylcyclohexane, 1,1-bis-(4-hydroxyphenyl)-3,5,5-trimethylcyclohexane, 1,1-bis-(4-hydroxyphenyl)-cyclododecane, 2,2-bis-(3,5-dimethyl-4-hydroxyphenyl)-propane, 4,4'-dihydroxybiphenyl ether and 4,4'-dihydroxy-biphenyl sulphide.

Preferred sulphonic acid derivatives are those of the formula

$$R^{13}-SO_2Cl \qquad (VII)$$

in which $R^{13}$ denotes straight-chain or branched $C_1$–$C_4$-alkyl, preferably methyl.

For the hydrogenation of the bissulphonates in dissolved form, 10 to 100 parts by weight, preferably 15 to 50 parts by weight, particularly preferably 15 to 20 parts by weight, per part by weight of the bissulphonate, of a $C_3$–$C_8$-ketone, a $C_3$–$C_8$-ester, a $C_4$–$C_8$-ether, a $C_2$–$C_8$- nitrile or pyridine or a mixture thereof are employed as the solvent. $C_3$-$C_8$-Ketones are, for example, acetone, methyl ethyl ketone, methyl propyl ketone, methyl butyl ketone, dimethyl ketone and others. $C_3$-$C_8$-esters are, for example, methyl acetate, ethyl acetate, butyl acetate, methyl butyrate, methyl benzoate and others. $C_4$-$C_8$-Ethers are, for example, diethyl ether, methyl tert.-butyl ether, tetrahydrofuran, dioxane, dibutyl ether and others. $C_2$-$C_8$-Nitriles are, for example, acetonitrile, propionitrile, butyronitrile, benzonitrile and others. Up to 50% of the total amount of this solvent can be replaced by a $C_1$-$C_4$-alcohol, for example by methanol, ethanol, propanol or butanol.

The $H_2$ pressure according to the invention is 1 to 100 bar, preferably 1 to 50 bar.

A support-containing or support-free hydrogenation catalyst in an amount of from 0.5 to 10 g, preferably 2 to 8 g, of hydrogenation-active component per mole of the bissulphonate is hydrogenated. The hydrogenation-active component may be a platinum metal, such as platinum, palladium or ruthenium, preferably palladium, or a base metal such as nickel, for example Raney nickel. Suitable supports are activated carbon, $SiO_2$, $Al_2O_3$, pumice and others. Both the hydrogenation-active components and the supports are known to those skilled in the art. In a preferential form, a platinum- or palladium-supported catalyst, particularly preferably a palladium/carbon catalyst (0.5-10% by weight of Pd, preferably 2-8% by weight of Pd) is employed.

The hydrogenation is carried out in a preferred manner such that the amount of catalyst is added in portions or continuously during the course of the hydrogenation.

Acylating agents are acid chlorides or acid anhydrides, such as acetyl chloride, acetic anhydride, propionyl chloride, butyryl chloride and others in the presence of Friedel-Crafts catalysts, such as aluminum chloride, iron chloride and others. Acylating agents and Friedel-Crafts catalysts of this type are known to those skilled in the art.

The oxidation of the acyl group to the carboxyl group can be carried out, for example, using a hypochlorite or hypobromite of potassium, sodium or calcium, preferably using sodium hypochlorite solution (bleaching liquor), in a basically known manner.

Examples of acids which can be prepared according to the invention are: 2,2-bis-(4-carboxyphenyl)-4-methylpentane, 3,3-bis-(4-carboxyphenyl)-5-methylheptane, 1,7-bis-(4-carboxyphenyl)-heptane, 1,3-bis-(4-carboxyphenyl)-cyclopentane, 1,3-bis-(4-carboxyphenyl)-cyclohexane, 1,4-bis-(4-carboxyphenyl)-cyclohexane, bis-(3,5-dimethyl-4-carboxyphenyl)-methane, 2,2-bis-(3,5-dimethyl-4-carboxyphenyl)-propane, 1,1-bis-(4-carboxyphenyl)-cyclopentane, 1,1-bis-(4-carboxyphenyl)-cyclohexane, 1,1-bis-(4-carboxyphenyl)-3-methylcyclohexane, 1,1-bis-(4-carboxyphenyl)-3,5,5-trimethylcyclohexane and 1,1-bis-(4-carboxyphenyl)-cyclododecane.

The process according to the invention may be represented, in the manner of an equation, as follows as exemplified by 2,2-bis-(4-hydroxyphenyl)-propane ("bisphenol A") using methanesulphonyl chloride, acetyl chloride and sodium hypochlorite:

Compound A
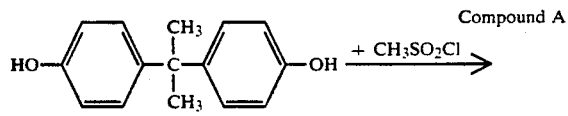

-continued

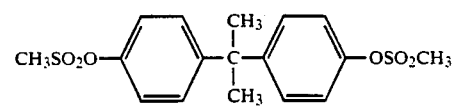

Compound B
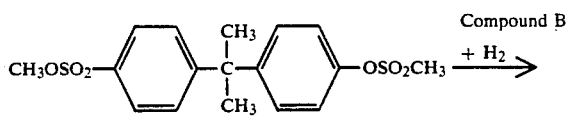

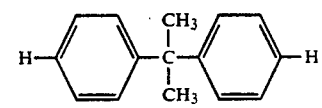

Compound C
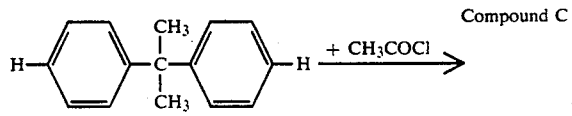

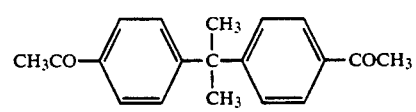

Compound D
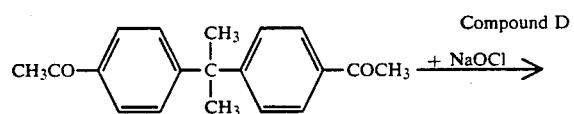

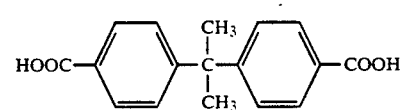

Compound E
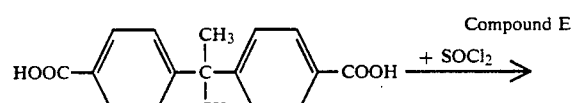

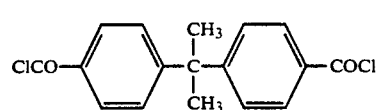

From the acids which can be prepared according to the invention, the acid chlorides (for example by reaction with thionyl chloride) or the esters (for example by direct esterification of the acid with alcohols, such as methanol or ethanol or by reaction of the acid chloride with alcohols of this type) can be prepared in a known manner, and can frequently be reacted more favourably than the free acids to give polymers.

Many of the acids which can be prepared according to the invention and also the dichlorides which can be prepared therefrom and the di-$C_1$-$C_4$-alkyl esters of these dicarboxylic acids are new. The invention therefore furthermore relates to aromatic dicarboxylic acids of the formula

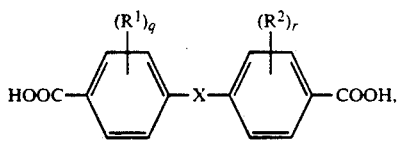 (VIII)

in which

X denote a single bond, $C_1$–$C_{12}$-alkylene, $C_2$–$C_{12}$-alkylidene, $C_5$–$C_{15}$-cycloalkylene, $C_5$–$C_{15}$-cycloalkylidene, oxygen, sulphur, the sulphone group, the group

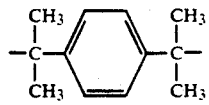

or the group

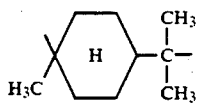

$R^1$ and $R^2$, independently of one another, denote straight-chain or branched $C_1$–$C_4$-alkyl and q and r, independently of one another, represent integers from 0 to 4, at least one of the indices q and r being different from 0 if X is a single bond, $C_1$–$C_6$-alkylene, linear $C_2$–$C_4$-alkylidene, linear $C_7$-alkylidene, 2,2-propylidene, oxygen, sulphur, the sulphone group, or the group

and to the dichlorides and the di-$C_1$–$C_4$-alkyl esters of these dicarboxylic acids, preferably the dicarboxylic acids themselves.

Among the new aromatic dicarboxylic acids of the formula (VI) may preferably be mentioned: 2,2-bis-(3,5-dimethyl-4-carboxyphenyl)-propane, 1,1-bis-(4-carboxyphenyl)-cyclohexane, 1,1-bis-(4-carboxyphenyl)-3-methylcyclohexane and 1,1-bis-(4-carboxyphenyl)-3,5,5-trimelhyl-cyclohexane.

The invention furthermore relates to a process for the preparation of the aromatic hydrocarbons of the above formula (V) as intermediates, which is characterized in that a) a bisphenol of the above formula (II) is reacted with a sulphonic acid derivative of the above formula (III) to give a bissulphonate of the above formula (IV) and b) the bissulphonate (IV) is hydrogenated in dissolved form at an $H_2$ pressure of 1–100 bar, preferably 1–50 bar, on a support-containing or support-free hydrogenation catalyst in an amount of from 0.5–10 g, preferably 2–8 g, of hydrogenation-active component per mole of bissulphonate (IV).

The invention also relates to the new aromatic hydrocarbons of the formula

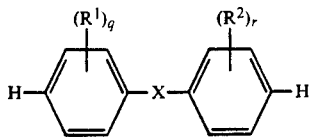 (IX)

in which $R^1$, $R^2$, x, q and r have the above meaning.

Among the new aromatic hydrocarbons (IX) may preferably be mentioned: 2,2-bis-(3,5-dimethyl-phenyl)-propane, 1,1-diphenyl-cyclohexane, 1,1-diphenyl-3-methylcyclohexane and 1,1-diphenyl-3,5,5-trimethyl-cyclohexane.

EXAMPLES

The process described in detail in the following as exemplified by 2,2-bis-(4-hydroxyphenyl)-propane can be used without substantial changes for all other bisphenols:

a) 2,2-Bis-(4-methylsulphonyloxy-phenyl)-propane (Compound A):

2 mol of 2,2-bis-(4-hydroxyphenyl)-propane were reacted at room temperature with 4.02 mol of methanesulphonyl chloride with the addition of 4 mol of triethylamine in methylene chloride. After aqueous work-up and crystallization from isopropanol, 83% of bissulphonate was obtained.

m.p.: 115°–116° C.

Analysis $C_{17}H_{20}O_6S_2$ calc.: C 53.1, H 5.2, S 16.6. found: C 53.1, H 5.2, S 16.6.

Analogously:

1,1-Bis-(4-methylsulphonyloxy-phenyl)-cyclohexane (81%):

m.p.: 114°–115° C.

Analysis $C_{20}H_{24}O_6S_2$ calc.: C 56.6, H 5.7, S 15.1. found: C 56.5, H 5.7, S 15.1.

Analogously:

1,1-Bis-(4-methanesulphonyloxy-phenyl)-3,5,5-trimethylcyclohexane (78%):

m.p.: 129°–131° C.

Analysis $C_{23}H_{30}O_6S_2$ calc.: C 59.2, H 6.4, S 13.7. found: C 59.2, H 6.4, S 13.7.

b) 2,2-Diphenylpropane (Compound B):

0.5 mol of Compound A were stirred at 40° C. and under 20 bar of $H_2$ in 3,000 ml of ethyl acetate with the addition of 27 g of palladium/carbon (5% Pd) and 1 mol of triethylamine; during the course of the reaction a further 15 g of Pd/C were added in total. After distillation, 84% of Compound B was obtained.

Analysis $C_{15}H_{16}$ calc.: C 91.8, H 8.2. found: C 91.8, H 8.2.

Analogously:

1,1-Diphenylcyclohexane (98%):

m.p.: 47° C.

Analysis $C_{18}H_{20}$ calc.: C 91.5, H 8.5. found: C 90.6, H 8.9.

MS: m/e 236 (74%).

Analogously:

1,1-Diphenyl-3,5,5-trimethyl-cyclohexane (72%):

Analysis $C_{21}H_{26}$ calc.: C 90.6, H 9.4. found: C 89.9, H 9.1.

MS: m/e 278 (92%).

c) 2,2-Bis-(4-acetyl-phenyl)-propane (Compound C):

0.8 mol of Compound B in 300 ml of ethylene chloride was added dropwise at 10° C. to a solution of 1.9 mol of aluminum chloride and 1.7 mol of acetyl chloride in 2 l of ethylene chloride and the mixture was subsequently stirred at room temperature for 15 hours. After aqueous work-up, the mixture was filtered through a frit filled with silica gel using petroleum ether/ethyl acetate. After separating off a forerun, 75% of Compound C was obtained.

MS: m/e 280 (35%).
m.p.: 73° C.
$^1$H-NMR (200 MHz, CDCl$_3$): $\delta$=7.88 (d, 4H); 7.30 (d, 4H); 2.58 (s, 6H); 1.72 (s, 6H).
Analogously:
1,1-Bis-(4-acetyl-phenyl)-cyclohexane (69%):
m.p.: 110°-113° C.
Analysis C$_{22}$H$_{24}$O$_2$ calc.: C 82.5, H 7.5. found: C 81.8, H 7.6.
MS: m/e 320 (40%).
Analogously:
1,1-Bis-(4-acetyl-phenyl)-3,5,5-trimethylcyclohexane (89%):
Analysis C$_{25}$H$_{30}$O$_2$ calc.: C 82.9, H 8.3. found: C 82.9, H 8.4.
MS: m/e 362 (29%).

d) 2,2-Bis-(4-carboxyphenyl)-propane (Compound D):

A solution of 0.35 mol of Compound C in 400 ml of dioxane were added dropwise at 20° to 25° C. to 1.5 l of bleaching powder liquor (1.85 mol/kg) and 100 g of NaOH. After 24 hours, the solution was washed with methylene chloride and the dicarboxylic acid D was isolated by acidifying and reprecipitating from NaOH (85%).

m.p.: >320° C.; IR (KBr): 2973, 1688, 1607, 1386, 1284 cm$^{-1}$.
Analogously:
1,1-Bis-(4-carboxyphenyl)-cyclohexane (85%):
m.p.: >320° C.
IR (KBr): 2938, 2862, 1691, 1284, 1606, 1386 cm$^{-1}$.
Analogously:
1,1-Bis-(4-hydroxyphenyl)-3,5,5-trimethylcyclohexane (72%):
m.p.: >320° C.
IR (KBr): 2952, 2927, 1692, 1607, 1388, 1283 cm$^{-1}$.

e) 2,2-Bis-(4-chlorocarbonylphenyl)-propane (Compound E):

0.5 mol of D were covered with an excess of thionyl chloride (250 ml), a few drops of pyridine were added and the mixture was heated to reflux until evolution of HCl was complete. Excess thionyl chloride was removed by distillation and the residue was distilled in a high vacuum or recrystallized from light petroleum. 73% of acid chloride was obtained.

b.p.: (0.15 mm): 198° C.
Analysis C$_{17}$H$_{14}$Cl$_2$O$_2$ calc.: C 63.5, H 4.4, Cl 22.1. found: C 63.6, H 4.5, Cl 21.6.
Analogously:
1,1-Bis-(4-chlorocarbonylphenyl)-cyclohexane (63%):
GC-MS: 99.5%, m/e 360/362/364 (14, 10, 1%).
Analogously:
1,1-Bis-(4-chlorocarbonylphenyl)-3,5,5-trimethylcyclohexane (74%):
GC-MS: 98.9% m/e 402/404/406 (8.5, 5.6, 1%).

f) 2,2-Bis-(4-methoxycarbonylphenyl)-propane 0.5 mol of 2,2-bis-(4-chlorocarbonyl-phenyl)-propane were stirred in 500 ml of abs. methanol with the addition of 2 g of triethylamine until the evolution of HCl was complete. The residue which remained after evaporation was recrystallized from a little methanol (yield 95%):

analysis: calc.: C 73.1%; H 6.5%, found: C 73.1%; H 6.4%.
$^1$H-NMR (200 MHz, CDCl$_3$): d=7.9 (4H); 7.3 (4H); 3.9 (6H); 1.7 (6H) ppm.

$$CH_3O-\overset{O}{\overset{\|}{C}}-\underset{}{\text{Ph}}-\underset{}{\text{Ph}}-\overset{O}{\overset{\|}{C}}-OCH_3$$

What is claimed is:

1. A process for the preparation of an aromatic dicarboxylic acid of the formula $$HOOC-\underset{(R_1)_m}{\text{Ph}}-X-\underset{(R_2)_n}{\text{Ph}}-COOH$$

in which
X denotes a single bond, C$_1$-C$_{12}$-alkylene, C$_5$-C$_{15}$-cycloalkylene, oxygen, sulphur,
or the group $$\text{cyclohexyl with } H, H_3C, \text{ and } -\overset{CH_3}{\underset{CH_3}{C}}-$$

R$_1$ and R$_2$, independently of one another denote straight-chain or branched C$_1$-C$_4$-alkyl or C$_1$-C$_4$-alkoxy and
m and n, independently of one another, represent integers from 0 to 4,
wherein
a) a bisphenol of the formula $$HO-\underset{(R_1)_m}{\text{Ph}}-X-\underset{(R_2)_n}{\text{Ph}}-OH$$

in which
R$_1$, R$_2$, m, n and X have the meaning mentioned, is reacted with a sulphonic acid derivative of the formula

R$_3$—SO$_2$—R$_4$ in which
R$_3$ represents straight-chain or branched C$_1$-C$_{12}$-alkyl, C$_3$-C$_8$-cycloalkyl, C$_6$-C$_{12}$-aryl or C$_7$-C$_{10}$-aralkyl and
R$_4$ is OH, Cl, Br or O-O$_2$S-R$_3$,
to give a bissulphonate of the formula $$R_3-SO_2O-\underset{(R_1)_m}{\text{Ph}}-X-\underset{(R_2)_n}{\text{Ph}}-OSO_2-R_3.$$

in which

R$_1$, R$_2$, R$_3$, m, n and X have the meaning mentioned, b) the bissulphonate obtained is hydrogenated in dissolved form at an H$_2$ pressure of 1 to 100 bar on a support-containing or support-free hydrogenation catalyst in an amount of from 0.5 to 10 g of hydrogenation-active component per mole of bissulphonate to give the corresponding hydrocarbon of the formula

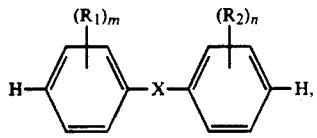

in which

R$_1$, R$_2$, x, m and n have the meaning mentioned, and c) the hydrocarbon obtained is doubly acylated and the acyl groups are oxidized to carboxyl groups.

2. The process of claim 1, wherein the hydrogenation of step b) is carried out under a H$_2$ pressure of 1 to 50 bar.

3. The process of claim 1, wherein the hydrogen catalyst is used in an amount of 2 to 8 g of hydrogenation-active component per mole of bissulphonate.

4. The process of claim 1, wherein the hydrogenation of step b) is carried out in a solvent from the group consisting of the C$_3$-C$_8$-ketones, the C$_3$-C$_8$-esters, the C$_4$-C$_8$-ethers, C$_2$-C$_8$-nitriles and pyridine in an amount of from 10 to 100 parts by weight per part by weight of the bissulphonate, it being possible to replace up to 50% of the total amount of the solvent by a C$_1$-C$_4$-alcohol.

5. The process of claim 4, wherein the solvent is used in an amount of from 15 to 50 parts by weight of the bissulphonate.

6. The process of claim 5, wherein the solvent is used in an amount of from 15 to 20 parts by weight of the bissulphonate.

7. The process of claim 1, wherein the hydrogenation catalyst is a supported catalyst containing 0.5 to 10% by weight of platinum metal.

8. The process of claim 1, wherein the hydrogenation catalyst is added in portions or continuously during the course of the hydrogenation.

9. The process of claim 1, wherein a bisphenol of the formula

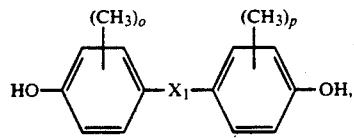

in which

X$_1$ denotes methylene and o and p, independently of one another, represent 0, 1 or 2, is employed.

10. The process of claim 1, wherein a sulphonic acid derivative of the formula

R$_{13}$—SO$_2$Cl, in which

R$_{13}$ denotes straight-chain or branched C$_1$-C$_4$-alkyl, is employed.

11. The process of claim 10, wherein R$_{13}$ denotes methyl.

12. An aromatic dicarboxylic acid of the formula

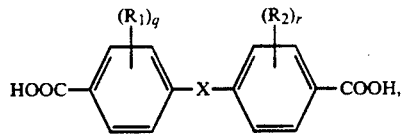

in which

X denotes a moiety selected from the group consisting of the formulae

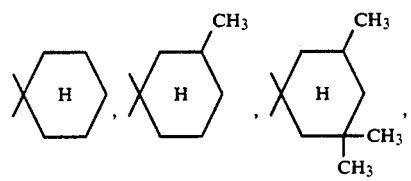

and the group

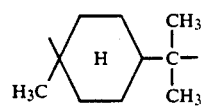

R$_1$ and R$_2$, independently of one another, denote straight-chain or branched C$_1$-C$_4$-alkyl and q and r, independently of one another, represent integers from 0 to 4, a dichloride or a di-C$_1$-C$_4$-alkyl ester of the dicarboxylic acid.

13. An aromatic dicarboxylic acid selected from the group consisting of 2,2-bis-(3,5-dimethyl-4-carboxyphenyl)-propane, 1,1-bis-(4-carboxyphenyl)-cyclohexane, 1,1-bis-(4-carboxyphenyl)-3-methyl-cyclohexane and 1,1-bis-(4-carboxyphenyl)-3,5,5-trimethyl-cyclohexane.

14. A process for the preparation of an aromatic hydrocarbon of the formula

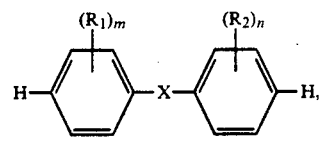

in which

X denotes a single bond, C$_1$-C$_{12}$-alkylene, C$_5$-C$_{15}$-cycloalkylene, oxygen, sulphur, or the group

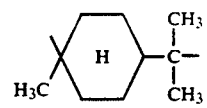

R$_1$ and R$_2$, independently of one another, denote straight-chain or branched C$_1$-C$_4$-alkyl or C$_1$-C$_4$-alkoxy and m and n, independently of one another, represent integers from 0 to 4, characterized in that a) a bisphenol of the formula

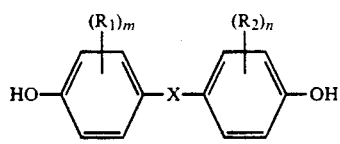

in which
R₁, R₂, m, n and X have the meaning mentioned, is reacted with the sulphonic acid derivative of the formula

R₃—SO₂—R₄, in which
R₃ represents straight-chain or branched $C_1$-$C_{12}$-alkyl, $C_3$-$C_8$-cycloalkyl, $C_6$-$C_{12}$-aryl or $C_7$-$C_{10}$-aralkyl and
R₄ is OH, Cl, Br or O-O₂S-R₃,
to give a bissulphonate of the formula

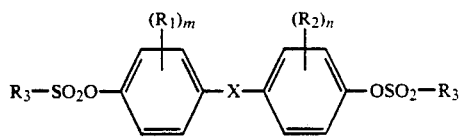

in which
R₁, R₂, R₃, m, n and X have the meaning mentioned, and b) the bissulphonate obtained is hydrogenated in dissolved form at an H₂ pressure of 1 to 100 bar on a support-containing or support-free hydrogenation catalyst in an amount of from 0.5 to 10 g of hydrogenation-active component per mole of bissulphonate.

15. An aromatic hydrocarbon of the formula

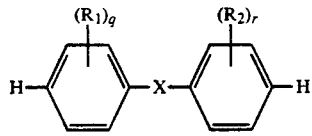

in which
X denotes or

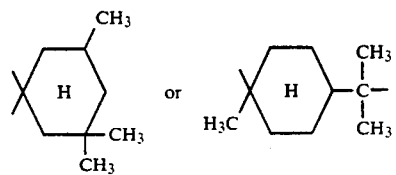

R₁ and R₂, independently of one another, denote straight-chain or branched $C_1$-$C_4$-alkyl and
q and r, independently of one another, represent integers from 0 to 4.

16. The aromatic hydrocarbon 1,1-diphenyl-3,5,5-trimethylcyclohexane.

* * * * *

UNITED STATES PATENT AND TRADEMARK OFFICE
CERTIFICATE OF CORRECTION

PATENT NO. : 5,183,926

DATED : February 2, 1993

INVENTOR(S) : Weider et al.

It is certified that error appears in the above-identified patent and that said Letters Patent is hereby corrected as shown below:

Title page, item [56] "U.S. Patent Documents: after "3,385,863 5/1968, Wick et al. ...delete " 563 " and substitute -- 562 --

Col. 9, line 38   Delete " 4-hydroxyphenyl " and substitute -- 4-carboxyphenyl --

Signed and Sealed this

First Day of March, 1994

Attest:

BRUCE LEHMAN

Attesting Officer

Commissioner of Patents and Trademarks